US010716830B2

(12) United States Patent
Frey

(10) Patent No.: US 10,716,830 B2
(45) Date of Patent: Jul. 21, 2020

(54) ERBB4 ACTIVATOR SCREENING ASSAY

(71) Applicant: Children's Hospital Los Angeles, Los Angeles, CA (US)

(72) Inventor: Mark R. Frey, Glendale, CA (US)

(73) Assignee: Children's Hospital Los Angeles, Los Angeles, CA (US)

( * ) Notice: Subject to any disclaimer, the term of this patent is extended or adjusted under 35 U.S.C. 154(b) by 0 days.

(21) Appl. No.: 15/984,194

(22) Filed: May 18, 2018

(65) Prior Publication Data

US 2018/0318391 A1 Nov. 8, 2018

Related U.S. Application Data

(60) Division of application No. 15/139,157, filed on Apr. 26, 2016, now abandoned, which is a continuation of application No. 14/236,831, filed as application No. PCT/US2012/050970 on Aug. 15, 2012, now Pat. No. 9,352,023.

(60) Provisional application No. 61/548,645, filed on Oct. 18, 2011, provisional application No. 61/523,733, filed on Aug. 15, 2011.

(51) Int. Cl.
| | | |
|---|---|---|
| *G01N 33/53* | (2006.01) | |
| *G01N 33/563* | (2006.01) | |
| *G01N 33/566* | (2006.01) | |
| *G01N 33/68* | (2006.01) | |
| *G01N 33/554* | (2006.01) | |
| *A61K 38/18* | (2006.01) | |
| *G01N 33/573* | (2006.01) | |

(52) U.S. Cl.
CPC ....... *A61K 38/1883* (2013.01); *G01N 33/573* (2013.01); *G01N 2333/71* (2013.01); *G01N 2440/14* (2013.01); *G01N 2500/10* (2013.01); *G01N 2800/065* (2013.01)

(58) Field of Classification Search
None
See application file for complete search history.

(56) References Cited

U.S. PATENT DOCUMENTS

| 6,544,759 | B1 | 4/2003 | Harari et al. |
| 7,094,882 | B2 | 8/2006 | Hariri et al. |
| 9,352,023 | B2 | 5/2016 | Frey |
| 2008/0008711 | A1 | 1/2008 | Schleyer et al. |
| 2010/0239654 | A1 | 9/2010 | Winter |
| 2014/0178404 | A1 | 6/2014 | Frey |
| 2016/0317619 | A1 | 11/2016 | Frey |
| 2018/0271944 | A1 | 9/2018 | Frey et al. |

FOREIGN PATENT DOCUMENTS

| JP | 2017109987 A | 6/2017 |
| WO | 2007014167 A2 | 2/2007 |
| WO | 2010060265 A1 | 6/2010 |
| WO | 2011006072 A2 | 1/2011 |
| WO | 2013025817 | 2/2013 |
| WO | 2014153385 A2 | 9/2014 |
| WO | 2017058828 A1 | 4/2017 |

OTHER PUBLICATIONS

Extended European Search Report of EP 16852432.0, dated Apr. 29, 2019, 5 Pages.
Aggarwal et al., Diverse Macrophage Populations Mediate Acute Lung Inflammation and Resolution, 2014, Am J Physiol Cell Mol Physiol, vol. 306, pp. L709-L725.
Baeck et al. Pharmacological Inhibition of the Chemokine C—C Motif Chemokine Ligand 2 (Monocyte Chemoattractant Protein 1) Accelerates Liver Fibrosis Regression by Suppressing Ly-6C+ Macrophage Infiltration in Mice., 2014, Hepatology vol. 59(3), pp. 1060-1072.
Bain et al., Resident and Pro-Inflammatory Macrophages in the Colon Represent Alternative Context-Dependent Fates of the Same Ly6Chi Monocyte Precursors., 2013, Mucosal Immunol vol. 6(3), pp. 498-510.
Blirando et al., Mast Cells are an Essential Component of Human Radiation Proctitis and Contribute to Experimental Colorectal Damage in Mice., 2011, Am. J. Pathol., 2011, vol. 178(2), pp. 640-651.
Boerma et al. Orazipone, a Locally Acting Immunomodulator, Ameliorates Intestinal Radiation Injury: A Preclinical Study in a Novel Rat Model., 2006, Int. J. Radiat. Oncol. Biol. Phys., vol. 66(2), pp. 552-559.
Eguchi et al., Macrophages and Islet Inflammation in Type 2 Diabetes, 2013, Diabetes Obes. Metab., vol. 15, Suppl 3, pp. 152-158.
Espinoza-Jimenez et al., Alternatively Activated Macrophages in Types 1 and 2 Diabetes, 2012, Mediators of Inflammation, Article ID 815953, 10 Pages.
Grainger et al., Macrophages in gastrointestinal homeostasis and inflammation, 2017, Pflugers Arch—Eur. J. Physiol., vol. 469(3-4), pp. 527-539.
Gregory et al., Macrophage Migration Inhibitory Factor Induces Macrophage Recruitment Via CC Chemokine Ligand 2, 2006, J. Immunol., vol. 177(11): 8072-8079.
Hayes et al., Innate Immune Responses to Bladder Infection., 2016, Microbiol. Spectr., vol. 4(6), 11 Pages.
Heinsbroek et al., The Role of Macrophages in Inflammatory Bowel Diseases, 2009, vol. 11, e14, 19 pages.
Hovdenak et al., Acute Radiation Proctitis: a Sequential Clinicopathologic Study during Pelvic Radiotherapy., 2000, Int. J. Radiat. Oncol. Biol. Phys., vol. 48(4), pp. 1111-1117.
Hovdenak et al., Clinical Significance of Increased Gelatinolytic Activity in the Rectal Mucosa during External Beam Radiation Therapy of Prostate Cancer, 2002, Int. J. Radiat. Oncol. Biol. Phys., vol. 53(4), pp. 919-927.

(Continued)

*Primary Examiner* — Christine J Saoud
*Assistant Examiner* — Jon M Lockard
(74) *Attorney, Agent, or Firm* — Nixon Peabody LLP

(57) ABSTRACT

The invention provides methods, pharmaceutical compositions and kits for treating, inhibiting and/or reducing the severity of inflammatory bowel disease and necrotizing enterocolitis in a subject in need thereof by administering an effective amount of a composition comprising an activator of ErbB4.

15 Claims, 10 Drawing Sheets

(56) References Cited

OTHER PUBLICATIONS

Li et al., Hepatic Macrophages in Liver Fibrosis: Pathogenesis and Potential Therapeutic Targets., 2016, BMJ open Gastroenterol, vol. 3, e000079, 4 Pages.
Lissner et al., Monocyte and M1 Macrophage-induced Barrier Defect Contributes to Chronic Intestinal Inflammation in IBD., 2015, Inflamm. Bowel Dis.,vol. 21(6), pp. 1297-1305.
Mahida YR, The Key Role of Macrophages in the Immunopathogenesis of Inflammatory Bowel Disease., 2000, Inflamm Bowel Dis, vol. 6(1), pp. 21-33.
Martin et al., Increased Expression of CCL2 in Insulin-Producing Cells of Transgenic Mice Promotes Mobilization of Myeloid Cells From the Bone Marrow, Marked Insulitis, and Diabetes, 2008, Diabetes, vol. 57(11), pp. 3025-3033.
Misharin et al., Monocyte-Derived Alveolar Macrophages Drive Lung Fibrosis and Persist in the Lung over the Life Span, 2017, J. Exp. Med., vol. 214(8), pp. 2387-2404.
Moore et al., Macrophages in Atherosclerosis: a Dynamic Balance, 2013, Nat Rev Immunol., vol. 13(10), pp. 709-721.
Peter J. Barnes, Inflammatory Mechanisms in Patients with Chronic Obstructive Pulmonary Disease, 2016, Journal of Allergy and Clinical Immunology, vol. 138(1), pp. 16-27.
Ren et al., Up-Regulation of Macrophage Migration Inhibitory Factor in Infants with Acute Neonatal Necrotizing Enterocolitis., 2005, Histopathology, 9 Pages.
Sun et al. Macrophage Phenotype in Liver Injury and Repair., 2017, Scand. J. Immunol. vol. 85(3), pp. 166-174.
Swirski et al., Ly-6Chi Monocytes DominateHypercholesterolemia-Associated Monocytosisand Give Rise to Macrophages in Atheromata, 2007, J Clin Invest, vol. 117, pp. 195-205.
Vlahos et al., Role of Alveolar Macrophages in Chronic Obstructive Pulmonary Disease, 2014, Front. Immunol., vol. 5, Article 435, 7 Pages.
Wan et al., M2 Kupffer Cells Promote M1 Kupffer Cell Apoptosis: A Protective Mechanism against Alcoholic and Nonalcoholic Fatty Liver Disease., 2014, Hepatology, vol. 59(1), pp. 130-142.
Wei et al., M1 to M2 Macrophage Polarization in HB-EGF Therapy for NEC, 2015, J. Surg. Res., vol. 197(1): 126-138.
Yamasaki et al., Lung Macrophage Phenotypes and Functional Responses: Role in the Pathogenesis of COPD, 2018, Int. J. Mol. Sci., vol. 19(582), 12 Pages.
Zhang et al., Kupffer Cells: Increasingly Significant Role in Nonalcoholic Fatty Liver Disease., 2014, Ann. Hepatol., vol. 13(5), pp. 489-495.
Bernard et al., Neuregulin-4 is a Survival Factor for Colon Epithelial Cells Both in Culture and in Vivo, 2012, The Journal of Biological Chemistry, vol. 287(47), pp. 39850-39858.
Wirtz, Chemically Induced Mouse Models of Intestinal Inflammation, 2007, Nature Protocols, vol. 2(3), pp. 541-546.
Schumacher, et al. Macrophage-Specific ErbB4 is Induced by DSS Colitis and Regulates Macrophage Survival, Presentation on Mar. 30, 2015 at Experimental Biology 2015 Meeting Held at Boston Convention & Exhibit Center, 15 Pages.
Schumacher, et al. Macrophage-Expressed ErbB4 is Protective Against Colitis, Presentation on May 17, 2015 at DDW Conference, Held at Walter E. Washington Convention Center, 17 Pages.
Schumacher, et al. Macrophage-Specific ErbB4 is Induced by DSS Colitis and Regulates Macrophage Survival, Abstract Accessible online in The FASEB Journal for the Experimental Biology 2015 Meeting, 3 Pages.
Schumacher, et al. ErbB4 Expression on Macrophages is Induced by DSS Colitis and Negatively Regulates Macrophage Survival, Abstract published in Apr. 2015 in Gastroenterology for the Digestive Disease Week 2015 conference, 2 Pages.
Parisi et al., Macrophage Polarization in Chronic Inflammatory Diseases: Killers or Builders?, 2018, Journal of Immunology Research, vol. 2018, Article ID 8917804, 25 Pages.
Guiteras et al., Macrophage in Chronic Kidney Disease, 2016, Clinical Kidney Journal, vol. 9(6), pp. 765-771.
Mcelroy et al., The ErbB4 Ligand Neuregulin-4 Protects against Experimental Necrotizing Enterocolitis, 2014, The American Journal of Pathology, vol. 184(10), pp. 2768-2778.
Yusta et al., ErbB Signaling is Required for the Proliferative Actions of GLP-2 in the Murine Gut, 2009, Gastroenterology, vol. 137, pp. 986-996.
Wang et al., The Brown Fat-Enriched Secreted Factor Nrg4 Preserves Metabolic Homeostatis through Attenuating Hepatic Lipogenesis, 2014, Nat. Med., vol. 20(12), pp. 1436-1443.
Mirzoeva et al, Single Administration of p2TA (AB103), a CD28 Antagonist Peptide, Prevents Inflammatory and Thrombotic Reactions and Protects against Gastrointestinal Injury in Total-Body Irradiated Mice, 2014, PLoS One, vol. 9(7):e101161, 8 Pages.
Paatero et al., ErbB4 and Its Isoforms: Patentable Drug Targets?, 2008, Recent Patents on DNA & Gene Sequences, vol. 2(1)., pp. 27-33.
Rannou et al, In Vivo Evidence for an Endothelium-Dependent Mechanism in Radiation-Induced Normal Tissue Injury, 2015, Scientific Reports, vol. 5(15738), 13 Pages.
International Search Report and Written Opinion of PCT Application No. PCT/US2012/050970, dated Jan. 24, 2013, 9 Pages.
PCT/US2012/050970 International Preliminary Report on Patentability dated Feb. 27, 2014; 7 pages.
Bueter et al. ErbB receptors in fetal endothelium—a potential linkage point for inflammation-associated neonatal disorders? Cytokine, Dec. 2006; vol. 36(5-6) pp. 267-275.
Ngo et al. Computational Complexity, Protein Structure Prediction, and the Levinthal Pardox. In Merz and Le Grand (Eds.) The Protein Folding Problem and Tertiary Structure Prediction. Birkhauser:Boston (1994) pp. 491-495.
Wells, J.A. Additivity of mutational effects in proteins. Biochemistry (1990). 29(37): 8509-8517.
Schumacher et al., "1089 Neuregulin-4 Stimulates Pro-Inflammatory Macrophage Apoptosis Through ADAM 17 Dependant Cleavage of ErbB4 to Ameliorate Colitis." [retrieved online Jan. 31, 2017 at http://www.gastrojournal.org/article/S0016-5085(16) 30804-6/abstract] Gastroenterology (Apr. 2016) vol. 150, Issue 4, Supplement 1, p. S217.
Naresh et al. "The ERBB4/HER4 Intracelluar Domain 4ICD is a BH3-Only Protein Promoting Apoptosis of Breast Cancer Cells." Cancer Research (2006). 66:(12): 6412-6420.
Hillard et al. "TNF—a converting enzyme-mediated ErbB4 transactivation by TNF promotes colonic epithelial cell survival." Am J Physiol Gastrointest Liver Physiol. (2011). 301(2):G338-46.
PCT/US2016/054027 International Search Report and Written Opinion dated Feb. 21, 2017; 11 pages.
EP 12824129.6 Extended Search Report dated May 4, 2017; 8 pages.
EP 19176250.9 Extended European Search Report dated Nov. 22, 2019, 8 pages.

A.

B.

C.

D.

D.

(i)

(ii)

p=0.0023
33% increase in survival time

ERBB4 ACTIVATOR SCREENING ASSAY

CROSS-REFERENCE TO RELATED APPLICATIONS

This application is a divisional of U.S. patent application Ser. No. 15/139,157 filed Apr. 26, 2016, now abandoned, which claims the benefit of priority under 35 U.S.C. § 120 as a continuation of U.S. patent application Ser. No. 14/236,831 filed Feb. 3, 2014, now issued as U.S. Pat. No. 9,352,023 on May 31, 2016, which is the National Phase of International Application No. PCT/US2012/050970 filed Aug. 15, 2012, which designated the U.S. and that International Application was published under PCT Article 21(2) in English, which claims priority under 35 U.S.C. § 119(e) to U.S. provisional patent application No. 61/548,645 filed Oct. 18, 2011, and U.S. provisional patent application No. 61/523,733 filed Aug. 15, 2011, the contents of each of which are herein incorporated by reference in their entirety.

STATEMENT REGARDING FEDERALLY SPONSORED RESEARCH OR DEVELOPMENT

This invention was made with government support under Grant Nos. DK077956 and DK090295 awarded by the National Institutes of Health. The government has certain rights in the invention.

FIELD OF INVENTION

The invention provides methods for treating inflammatory bowel disease and necrotizing enterocolitis in a subject in need thereof using activators of ErbB4.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

ErbB4 is the least well-understood member of the family of receptor tyrosine kinases which also includes EGF receptor (EGFR/ErbB1), ErbB2/HER2, and ErbB3 (Wieduwilt, M. J., and Moasser, M. M. (2008) *Cellular and molecular life sciences: CMLS* 65, 1566-1584). ErbBs recognize and are activated by a suite of ligands including heparin-binding EGF-like growth factor (HB-EGF), betacellulin, and the heregulin/neuregulin family (Wilson, K. J., Gilmore, J. L., Foley, J., Lemmon, M. A., and Riese, D. J., 2nd. (2009) *Pharmacology & therapeutics* 122, 1-8). Ligand binding is associated with receptor dimerization, increased tyrosine kinase activity, and auto-phosphorylation on c-terminal tyrosine residues, which then provide docking sites for downstream effectors (Bublil, E. M., and Yarden, Y. (2007) *Current opinion in cell biology* 19, 124-134). Different ligands show distinct specificities and affinities for different ErbB receptors, and stimulate diverse dimerization patterns, signaling, and cellular responses (Saito, T., Okada, S., Ohshima, K., Yamada, E., Sato, M., Uehara, Y., Shimizu, H., Pessin, J. E., and Mori, M. (2004) *Endocrinology* 145, 4232-4243; Sweeney, C., Lai, C., Riese, D. J., 2nd, Diamonti, A. J., Cantley, L. C., and Carraway, K. L., 3rd. (2000) *J Biol Chem* 275, 19803-19807).

ErbB4 has several features which distinguish it from other tyrosine kinases, making it a unique target both in terms of signaling and potential role in human disease. It can bind both heregulin/neuregulin growth factors and a subset of EGF-family factors (Jones, J. T., Akita, R. W., and Sliwkowski, M. X. (1999) *FEBS letters* 447, 227-231), but at least one peptide ligand—NRG4—is exclusive to ErbB4 and does not bind ErbB1-3 (Haran, D., Tzahar, E., Romano, J., Shelly, M., Pierce, J. H., Andrews, G. C., and Yarden, Y. (1999) *Oncogene* 18, 2681-2689). Furthermore, ErbB4 associates with a divergent and more restricted suite of SH2-containing targets than EGFR, ErbB2, or ErbB3 (Kaushansky, A., Gordus, A., Budnik, B. A., Lane, W. S., Rush, J., and MacBeath, G. (2008) *Chem Biol* 15, 808-817). Thus, selective ErbB4 activation with NRG4 may elicit different cellular outcomes than stimulation with other EGF-like or heregulin family molecules.

ErbB4 is induced in colonic epithelial cells by inflammatory cytokines, and is present at elevated levels in the inflamed colonic mucosa of IBD patients (Frey, M. R., Edelblum, K. L., Mullane, M. T., Liang, D., and Polk, D. B. (2009) *Gastroenterology* 136, 217-226). This appears to be a compensatory protective response rather than a pathological process, as ectopic ErbB4 overexpression protects cultured mouse colon epithelial cells from cytokine-induced apoptosis in a ligand-dependent manner (Frey, M. R., Edelblum, K. L., Mullane, M. T., Liang, D., and Polk, D. B. (2009) *Gastroenterology* 136, 217-226; Hilliard, V. C., Frey, M. R., Dempsey, P. J., Peek, R. M., Jr., and Polk, D. B. (2011) *American journal of physiology. Gastrointestinal and liver physiology* 301, G338-346; Frey, M. R., Hilliard, V. C., Mullane, M. T., and Polk, D. B. (2010) *Laboratory Investigation* 90, 1415-1424). However, these studies, like most investigation of ErbB4 function, used shared ErbB ligands heregulin(HRG)-1β or HB-EGF, raising the question of signal specificity.

Crohn's disease and ulcerative colitis, collectively known as IBD, together affect more than 1.4 million American patients (Strober, W., Fuss, I., and Mannon, P. (2007) *J Clin Invest* 117, 514-521). The causes and cures of IBD remain elusive, but it is clear that a general feature of the pathology of these disorders is elevated apoptosis in the intestinal epithelium (Qiu, W., Wu, B., Wang, X., Buchanan, M. E., Regueiro, M. D., Hartman, D. J., Schoen, R. E., Yu, J., and Zhang, L. (2011) *J Clin Invest* 121, 1722-1732; Di Sabatino, A., Ciccocioppo, R., Luinetti, O., Ricevuti, L., Morera, R., Cifone, M. G., Solcia, E., and Corazza, G. R. (2003) *Diseases of the colon and rectum* 46, 1498-1507), driven by inflammatory cytokines such as TNF and IFN-γ. Thus, identifying signal transduction pathways which protect colon epithelial cells from cytokine- or injury-induced apoptosis will lead to new methods to control disease flares.

Current therapies for inflammatory bowel disease include anti-TNF therapies and steroid anti-inflammatories and are generally aimed at interrupting inflammation rather than specifically promoting mucosal healing. These therapies have shown limited effectiveness.

In the instant invention, the inventor proposes alternative therapies for treating inflammatory bowel disease.

Necrotizing enterocolitis is a disease condition in which portions of the bowel undergo tissue necrosis. It is predominant in premature infants, wherein the timing of its onset is generally inversely proportional to the gestational age of the baby at birth. Current treatments include using an IV catheter to provide nutrients, antibiotic therapy to treat infections, surgery etc. Herein, the inventor provides an alternative therapy for treating necrotizing enterocolitis.

DETAILED DESCRIPTION OF THE INVENTION

Figure 1:
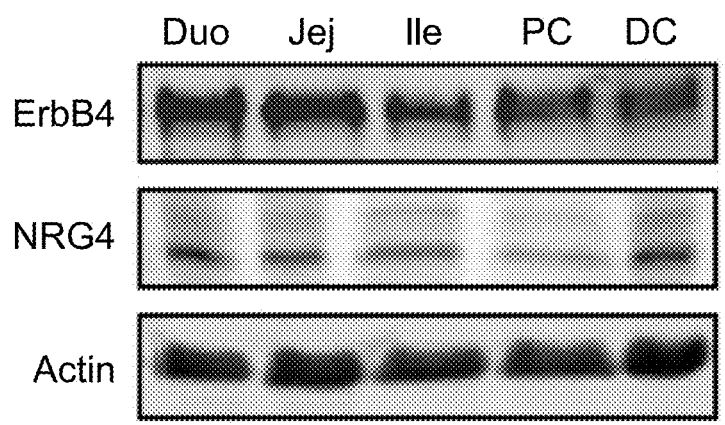
FIG. 1 depicts, in accordance with an embodiment of the invention that (A) ErbB4 and NRG4 are expressed throughout the intestinal tract and (B) NRG4 blocks cytokine-induced apoptosis in cultured colon epithelial cells
Figure 1:
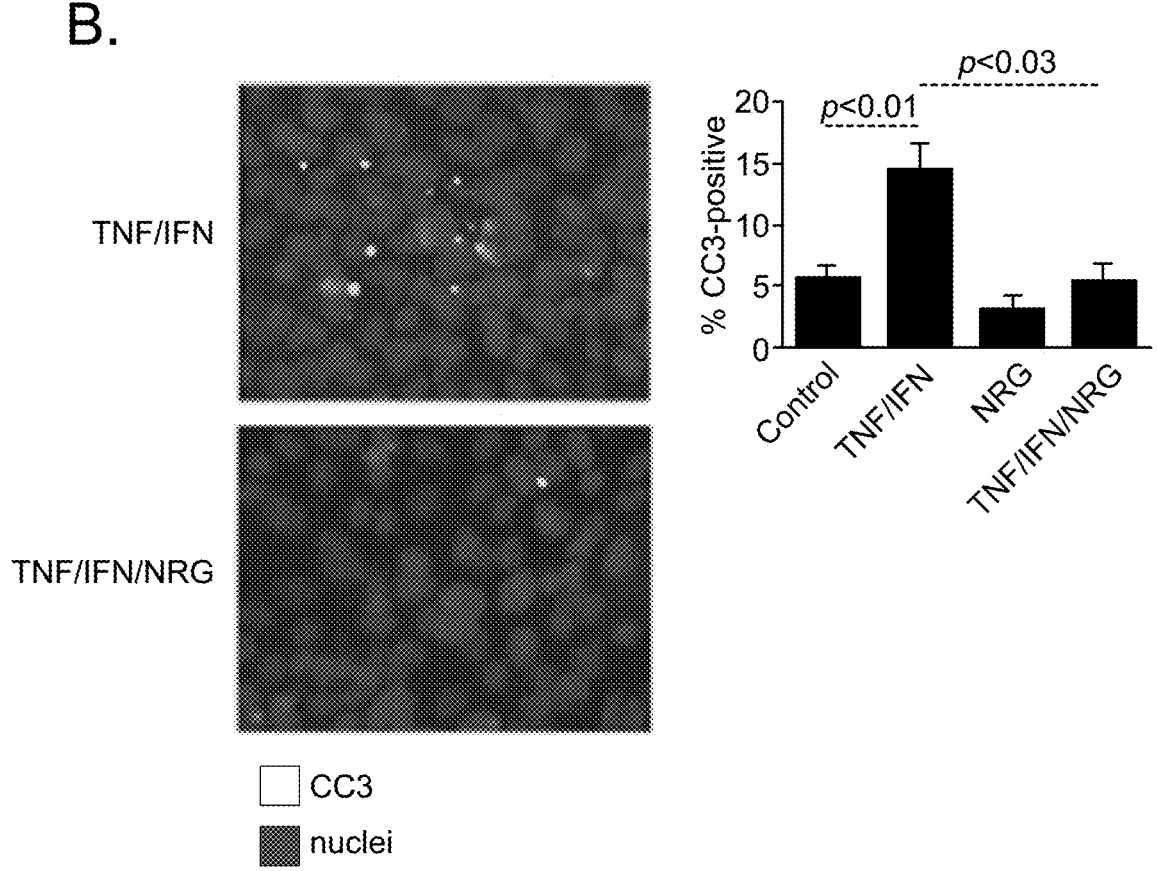

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Beneficial results" may include, but are in no way limited to, lessening or alleviating the severity of the disease condition, preventing the disease condition from worsening, curing the disease condition, preventing the disease condition from developing, lowering the chances of a patient developing the disease condition and prolonging a patient's life or life expectancy. In some embodiments, the disease condition is cancer.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

"Treatment" and "treating," as used herein refer to both therapeutic treatment and prophylactic or preventative measures, wherein the object is to prevent or slow down (lessen) the targeted pathologic condition, prevent the pathologic condition, pursue or obtain beneficial results, or lower the chances of the individual developing the condition even if the treatment is ultimately unsuccessful. Those in need of treatment include those already with the condition as well as those prone to have the condition or those in whom the condition is to be prevented.

"Inflammatory Bowel Disease" or "IBD" as used herein refers to the inflammatory conditions including but not limited to Crohn's disease, ulcerative colitis, collagenous colitis, lymphocytic colitis, ischaemic colitis, diversion colitis, Behçet's disease and indeterminate colitis.

The inventor proposes an alternative to existing therapies for treating inflammatory bowel disease comprising administering an effective amount of an ErbB4 activator to the subject. As described herein, ErbB4 is activated by Neuregulin-4 (NRG4). NRG4 is the only known growth factor found in the intestine which is entirely specific for ErbB4 receptor tyrosine kinase. Inventor's data indicates that NRG4-ErbB4 signaling is an anti-apoptotic pathway in colon epithelial cells which is compromised in colitis by loss of NRG4 ligand. While not wishing to be bound by a specific theory, the inventor hypothesizes that ErbB4 activation by NRG4 promotes colon epithelial cell survival and protects the epithelium from inflammation-induced damage.

Therapeutic Methods of the Invention

The invention provides methods for treating, inhibiting, reducing the symptoms of and/or promoting prophylaxis of diseases associated with apoptosis induced by cytokines such as TNF and IFN-α. In some embodiments, the methods include administering to the subject an activator of ErbB4. Examples of diseases include but are not limited to inflammatory bowel disease, necrotizing enterocolitis, rheumatoid arthritis and asthma. In some embodiments, the activator of ErbB4 is selected from the group consisting of a small molecule, a peptide, an antibody or a fragment thereof and a nucleic acid molecule. In one embodiment, the ErbB4 activator is Neuregulin-4 or a pharmaceutical equivalent, analog, derivative or a salt thereof.

The invention provides therapeutic methods for treating, inhibiting, reducing the symptoms of and/or promoting prophylaxis of inflammatory bowel disease in a subject in need thereof using activators of ErbB4.

The invention also provides therapeutic methods for treating, inhibiting, reducing the symptoms of and/or promoting prophylaxis of necrotizing enterocolitis in a subject in need thereof using activators of ErbB4.

Inflammatory Bowel Disease and ErbB4 Activator

The invention provides methods for treating inflammatory bowel disease in a subject in need thereof. The methods comprise providing a composition comprising an activator of ErbB4 and administering an effective amount of the composition to the subject so as to treat inflammatory bowel disease in the subject. In some embodiments, the activator of ErbB4 is selected from the group consisting of a small molecule, a peptide, an antibody or a fragment thereof and a nucleic acid molecule. In one embodiment, the ErbB4 activator is Neuregulin-4 or a pharmaceutical equivalent, analog, derivative or a salt thereof.

The invention also provides methods for inhibiting and/or reducing symptoms of inflammatory bowel disease in a subject in need thereof. The methods comprise providing a composition comprising an activator of ErbB4 and administering an effective amount of the composition to the subject so as to inhibit and/or reduce symptoms of, inflammatory bowel disease in the subject. In some embodiments, the activator of ErbB4 is selected from the group consisting of a small molecule, a peptide, an antibody or a fragment thereof and a nucleic acid molecule. In one embodiment, the ErbB4 activator is Neuregulin-4 or a pharmaceutical equivalent, analog, derivative or a salt thereof.

The invention also provides methods for inhibiting inflammation-associated death of small intestinal and colonic epithelial cells in a subject in need thereof. The methods comprise providing a composition comprising an activator of ErbB4 and administering an effective amount of the composition to the subject so as to inhibit inflammation-associated death of small intestinal and colonic epithelial cells in a subject. In some embodiments, the activator of ErbB4 is selected from the group consisting of a small molecule, a peptide, an antibody or a fragment thereof and a nucleic acid molecule. In one embodiment, the ErbB4 activator is Neuregulin-4 or a pharmaceutical equivalent, analog, derivative or a salt thereof.

The invention also provides methods for promoting the prophylaxis of inflammatory bowel disease, mitigating the effect of inflammatory bowel disease, reducing the severity of inflammatory bowel disease, reducing the likelihood of developing inflammatory bowel disease and/or slowing the progression of inflammatory bowel disease in subjects in need thereof. The methods comprise providing a composition comprising an activator of ErbB4 and administering a therapeutically effective amount of the composition to the subject so as to promote the prophylaxis of inflammatory bowel disease, mitigate the effect of inflammatory bowel disease, reduce the severity of inflammatory bowel disease, reduce the likelihood of developing inflammatory bowel disease and/or slow the progression of inflammatory bowel disease in subjects in need thereof. In some embodiments, the activator of ErbB4 is selected from the group consisting of a small molecule, a peptide, an antibody or a fragment thereof and a nucleic acid molecule. In one embodiment, the ErbB4 activator is Neuregulin-4 or a pharmaceutical equivalent, analog, derivative or a salt thereof.

In various embodiments, the ErbB4 activator may be used in conjunction with existing treatments for inflammatory bowel disease. For example, ErbB4 activators may be used in conjunction with existing therapies such as diet modifications and administrations of therapeutic drugs including but not limited to sulfasalazine (Azulfadine), mesalamine (Asacol, Pentasa), azathioprine (Imuran), 6-MP (Purinethol), cyclosporine, methotrexate, infliximab (Remicade), Budesonide (Entocort EC) and corticosteroids (prednisone), so as to treat inflammatory bowel disease. Dosages of existing therapies that may be used with the ErbB4 activators will be apparent to one skilled in the art. In one embodiment, the ErbB4 activator is Neuregulin-4 or a pharmaceutical equivalent, analog, derivative or a salt thereof.

Colorectal cancer represents the major cause for excess morbidity and mortality by malignant disease in ulcerative colitis as well as in Crohn's disease. In an embodiment, treatment, inhibition or reduction of symptoms of inflammatory bowel disease in a subject may prevent and/or treat colorectal cancer. Accordingly, the invention provides methods for treating, reducing the severity of and/or preventing colorectal cancer in a subject in need thereof. The methods comprise providing a composition comprising an activator of ErbB4 and administering an effective amount of the composition to the subject so as to inhibit inflammation-associated death of small intestinal and colonic epithelial cells in a subject. In some embodiments, the activator of ErbB4 is selected from the group consisting of a small molecule, a peptide, an antibody or a fragment thereof and a nucleic acid molecule. In one embodiment, the ErbB4 activator is Neuregulin-4 or a pharmaceutical equivalent, analog, derivative or a salt thereof.

In some embodiments, the activator of ErbB4 is a direct activator of ErbB4 such that the activator binds ErbB4 and activates it by, for example, inducing or increasing phosphorylation of ErbB4. In some embodiments, the activator of ErbB4 is an indirect activator of ErbB4 such that the activator inhibits the inhibitor of ErbB4 so that ErbB4 is activated.

Necrotizing Enterocolitis and ErbB4 Activator

The invention provides a method for treating necrotizing enterocolitis in a subject in need thereof. The method comprises providing a composition comprising an activator of ErbB4 and administering a therapeutically effective amount of the composition to the subject so as to treat necrotizing enterocolitis. In some embodiments, the activator of ErbB4 is selected from the group consisting of a small molecule, a peptide, an antibody or a fragment thereof and a nucleic acid molecule. In one embodiment, the ErbB4 activator is Neuregulin-4 or a pharmaceutical equivalent, analog, derivative or a salt thereof.

The invention also provides a method for inhibiting necrotizing enterocolitis in a subject in need thereof. The method comprises providing a composition comprising an activator of ErbB4 and administering a therapeutically effective amount of the composition to the subject so as to inhibit necrotizing enterocolitis. In one embodiment, the ErbB4 activator is NRG4, a salt thereof, or a pharmaceutical equivalent thereof. In some embodiments, the activator of ErbB4 is selected from the group consisting of a small molecule, a peptide, an antibody or a fragment thereof and a nucleic acid molecule. In one embodiment, the ErbB4 activator is Neuregulin-4 or a pharmaceutical equivalent, analog, derivative or a salt thereof.

The invention also provides methods for promoting the prophylaxis of necrotizing enterocolitis, mitigating the effect of necrotizing enterocolitis, reducing the severity of necrotizing enterocolitis, reducing the likelihood of developing necrotizing enterocolitis and/or slowing the progression of necrotizing enterocolitis in subjects in need thereof. The methods comprise providing a composition comprising an activator of ErbB4 and administering a therapeutically effective amount of the composition to the subject so as to inhibit necrotizing enterocolitis. In some embodiments, the activator of ErbB4 is selected from the group consisting of a small molecule, a peptide, an antibody or a fragment thereof and a nucleic acid molecule. In one embodiment, the ErbB4 activator is Neuregulin-4 or a pharmaceutical equivalent, analog, derivative or a salt thereof.

In some embodiments, the activator of ErbB4 is a direct activator of ErbB4 such that the activator binds ErbB4 and activates it by, for example, inducing or increasing phosphorylation of ErbB4. In some embodiments, the activator of ErbB4 is an indirect activator of ErbB4 such that the activator inhibits the inhibitor of ErbB4 so that ErbB4 is activated.

Additionally, in case of necrotizing enterocolitis, ErbB4 activators may be used in conjunction with existing treatments such as stopping enteral feedings, performing nasogastric decompression, and initiating broad-spectrum antibiotics. In one embodiment, the ErbB4 activator is Neuregulin-4 or a pharmaceutical equivalent, analog, derivative or a salt thereof.

Various methods may be utilized to administer the composition of the claimed methods, including but not limited to aerosol, nasal, oral, transmucosal, transdermal, parenteral, implantable pump, continuous infusion, topical application, capsules and/or injections.

The subjects treated by the present invention include mammalian subjects, including, human, monkey, ape, dog, cat, cow, horse, goat, pig, rabbit, mouse and rat.

Dosages of the Invention

As described above, in various embodiments of the invention, the ErbB4 activator may be used in conjunction with existing treatments for inflammatory bowel disease and necrotizing enterocolitis. In some embodiments, the ErbB4 activator is administered concurrently with the existing treatments for inflammatory bowel disease and necrotizing enterocolitis. In various embodiments, the ErbB4 activator is administered sequentially with the existing treatments for inflammatory bowel disease and necrotizing enterocolitis. The ErbB4 activator alone or in conjunction with the existing treatments for inflammatory bowel disease and necrotizing enterocolitis, may be administered at various stages of inflammatory bowel disease and necrotizing enterocolitis, such as early stages, middle stages and/or late stages of inflammatory bowel disease and necrotizing enterocolitis. In one embodiment, the ErbB4 activator is Neuregulin-4 or a pharmaceutical equivalent, analog, derivative or a salt thereof.

In some embodiments of the invention, the effective amount of ErbB4 activator in the composition can be in the range of about 10-50 mg/day, 50-100 mg/day, 100-150 mg/day, 150-200 mg/day, 100-200 mg/day, 200-300 mg/day, 300-400 mg/day, 400-500 mg/day, 500-600 mg/day, 600-700 mg/day, 700-800 mg/day, 800-900 mg/day, 900-1000 mg/day, 1000-1100 mg/day, 1100-1200 mg/day, 1200-1300 mg/day, 1300-1400 mg/day, 1400-1500 mg/day, 1500-1600 mg/day, 1600-1700 mg/day, 1700-1800 mg/day, 1800-1900 mg/day, 1900-2000 mg/day, 2000-2100 mg/day, 2100-2200 mg/day, 2200-2300 mg/day, 2300-2400 mg/day, 2400-2500 mg/day, 2500-2600 mg/day, 2600-2700 mg/day, 2700-2800 mg/day, 2800-2900 mg/day or 2900-3000 mg/day. In one embodiment of the invention, the ErbB4 is Neuregulin-4 or a pharmaceutical equivalent, analog, derivative or a salt thereof.

In further embodiments of the invention, the effective amount of activator of ErbB4 for use with the claimed methods may be in the range of 0.001-0.005 mg/kg, 0.005-0.01 mg/kg, 0.01-0.02 mg/kg, 0.02-0.04 mg/kg, 0.04-0.06 mg/kg, 0.06-0.08 mg/kg, 0.08-1 mg/kg, 1-5 mg/kg, 5-10 mg/kg, 10-15 mg/kg, 15-20 mg/kg, 20-25 mg/kg, 25-30 mg/kg, 30-35 mg/kg, 35-40 mg/kg, 40-45 mg/kg, 45-50 mg/kg, 10-50 mg/kg, 50-100 mg/kg, 100-150 mg/kg, 150-200 mg/kg, 100-200 mg/kg, 200-300 mg/kg, 300-400 mg/kg, 400-500 mg/kg, 500-600 mg/kg, 600-700 mg/kg, 700-800 mg/kg, 800-900 mg/kg, 900-1000 mg/kg, 1000-1100 mg/kg, 1100-1200 mg/kg, 1200-1300 mg/kg, 1300-1400 mg/kg, 1400-1500 mg/kg, 1500-1600 mg/kg, 1600-1700 mg/kg, 1700-1800 mg/kg, 1800-1900 mg/kg, 1900-2000 mg/kg, 2000-2100 mg/kg, 2100-2200 mg/kg, 2200-2300 mg/kg, 2300-2400 mg/kg, 2400-2500 mg/kg, 2500-2600 mg/kg, 2600-2700 mg/kg, 2700-2800 mg/kg, 2800-2900 mg/kg or 2900-3000 mg/kg. In one embodiment of the invention, the ErbB4 activator is Neuregulin-4 or a pharmaceutical equivalent, analog, derivative or a salt thereof.

Typical dosages of an effective amount of an ErbB4 activator, such as Neuregulin-4, can be in the ranges recommended by the manufacturer where known therapeutic compounds are used, and also as indicated to the skilled artisan by the in vitro responses or responses in animal models. The actual dosage can depend upon the judgment of the physician, the condition of the patient, and the effectiveness of the therapeutic method based, for example, on the in vitro responsiveness of relevant cultured cells or histocultured tissue sample, or the responses observed in the appropriate animal models.

Screening Methods of the Invention

Another aspect of the invention relates to assays and methods for identifying compounds that activate ErbB4. In one embodiment, the method comprises contacting ErbB4 in an ErbB4 positive cell with the compound of interest and subsequently determining whether the contact results in altered phosphorylation of ErbB4. In an embodiment, an alteration in the amount phosphorylation of ErbB4 is an increase in the amount of phosphorylation of ErbB4. In one embodiment, an increase in the amount of phosphorylation of ErbB4 indicates that the molecule of interest is an activator of ErbB4.

Screening methods of the invention further provide methods for identifying compounds that activate ErbB4 wherein the method includes contacting ErbB4 in an ErbB4 positive cell with the compound of interest, contacting the ErbB4 positive cell and the compound of interest with a target cell and subsequently determining whether the contact results in altered apoptosis of target cells. In an embodiment, a decrease in apoptosis of target cells indicates that the molecule of interest is an activator of ErbB4.

The compound of interest that activates ErbB4 may be any one or more of a small molecule, a peptide, a polypeptide, an antibody or a fragment thereof and a nucleic acid molecule.

Assays that may be employed to identify compounds that activate ErbB4 include but are not limited to any one or more of microarray assay, quantitative PCR, Northern blot assay, Southern blot assay, Western blot assay immunohistochemical assays, binding assays, gel retardation assays, assays using yeast two-hybrid systems, assays that measure cell apoptosis, or a combination thereof. A person skilled in the art can readily employ numerous techniques known in the art to determine whether a particular agent activates ErbB4.

Pharmaceutical Compositions

In various embodiments, the present invention provides pharmaceutical compositions including a pharmaceutically acceptable excipient along with a therapeutically effective amount of an ErbB4 activator, such as Neuregulin-4 or a pharmaceutical equivalent, analog, derivative or a salt thereof. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including, but not limited to aerosol, nasal, oral, transmucosal, transdermal or parenteral.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical composition according to the invention can also be bead system for delivery for the ErbB4 activator to the target cells. For example, pectin/zein hydrogel bead system may be used to deliver Neuregulin-4 or a pharmaceutical equivalent, analog, derivative or a salt thereof, to the target cells in the subject (Yan F. et al., *J Clin Invest.* 2011 June; 121(6):2242-53).

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The Science and Practice of Pharmacy* (Gennaro ed. 20th edition, Williams & Wilkins PA, USA) (2000).

Kits of the Invention

The present invention is also directed to kits to treat inflammatory bowel disease and/or necrotizing colitis. The kit is an assemblage of materials or components, including at least one of the inventive compositions. Thus, in some embodiments the kit contains a composition including an ErbB4 activator, such as Neuregulin-4 or a pharmaceutical equivalent, analog, derivative or a salt thereof, as described above.

The exact nature of the components configured in the inventive kit depends on its intended purpose. In one embodiment, the kit is configured particularly for human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to treat or prevent inflammatory bowel disease and/or necrotizing colitis in a subject. Optionally, the kit also contains other useful components, such as, measuring tools, diluents, buffers, pharmaceutically acceptable carriers, syringes or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be a bottle used to contain suitable quantities of an inventive composition containing an ErbB4 activator, such as Neuregulin-4 or a pharmaceutical equivalent, analog, derivative or a salt thereof. The packaging material generally has an external label which indicates the contents and/or purpose of the kit and/or its components.

EXAMPLES

The following example is provided to better illustrate the claimed invention and is not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Expression of the ErbB4 tyrosine kinase is elevated in colonic epithelial cells during inflammatory bowel disease (IBD), while ErbB4 overexpression in cultured colonocytes blocks TNF-induced apoptosis in a ligand-dependent manner. Together these observations suggest that ErbB4 induction may be a protective response. However, the effects of ErbB4 signaling in the colonic epithelium in vivo were not known. Furthermore, previous work on ErbB4 used ligands shared with other receptors, raising the question of whether observed responses are explicitly due to ErbB4. Herein, the inventor used the ErbB4-specific ligand neuregulin-4 (NRG4) to activate ErbB4 and define its role in colonocyte biology. Treatment with NRG4, either in cultured cells or in mice, blocked colonic epithelial apoptosis induced by TNF and IFN-γ. NRG4 stimulated phosphorylation of ErbB4 but not of other ErbB receptors, indicating that this is a specific response. Furthermore, in contrast to related ligands, NRG4 enhanced cell survival but not proliferation or migration, and stimulated phosphorylation of the anti-apoptotic mediator Akt but not ERK MAPK. Pharmacological inhibition of PI3K/Akt signaling reversed NRG4's anti-apoptotic effects, confirming the role of this cascade in NRG4-induced cell survival. With regard to the potential clinical importance of this pathway, NRG4 expression was decreased in human IBD samples and mouse models of colitis, suggesting that activation of ErbB4 is altered in disease. Thus, exogenous NRG4 may be beneficial for disorders in which epithelial apoptosis is part of the pathology.

Example 1

Experimental Methods

Cell Culture—

Conditionally immortalized, non-transformed young adult mouse colon (YAMC) epithelial cells were provided by Dr. Robert Whitehead (Whitehead, R. H., VanEeden, P. E., Noble, M. D., Ataliotis, P., and Jat, P. S. (1993) *Proc Natl Acad Sci USA* 90, 587-591). These cells express low levels of endogenous ErbB4; YAMC-B4 cells expressing a human ErbB4 construct were generated as previously described (Frey, M. R., Edelblum, K. L., Mullane, M. T., Liang, D., and Polk, D. B. (2009) *Gastroenterology* 136, 217-226). Cell pools showing no autocrine ErbB4 activation were selected for use and maintained under permissive conditions [33° C. in RPMI 1640 with 5% FBS, 5 units/ml mouse interferon-γ (Peprotech, Rocky Hill, N.J.), 100 U/ml penicillin and streptomycin, 5 µg/ml insulin, 5 µg/ml transferrin, and 5 ng/ml selenous acid (BD Biosciences, San Jose, Calif.)], then shifted to nonpermissive conditions (RPMI 1640 containing 0.5% FBS, streptomycin and penicillin without IFN-γ, insulin, transferrin, or selenous acid, at 37° C.) overnight before use in experiments.

Antibodies, Cytokines, Growth Factors, and Inhibitors—

Antibodies were purchased from: monoclonal anti-actin, Sigma Corp. (St. Louis, Mo.); polyclonal anti-phospho-Y1284 ErbB4, phospho-Y1068 EGFR, phospho-Y1248 ErbB2, phospho-Y1289 ErbB3, EGFR, ErbB2, ErbB3, phospho-S473 Akt, cleaved caspase-3, cleaved poly (ADP-ribose) polymerase, phospho-p38, and phospho-ERK, Cell Signaling (Danvers, Mass.); polyclonal anti-ErbB4 (c-18) and goat polyclonal anti-COX-2, Santa Cruz Biotechnology (Santa Cruz, Calif.); anti-Ki67, Dako Corp (Carpinteria, Calif.); IRDye anti-mouse, anti-rabbit, and anti-goat, Li-Cor Corp (Lincoln, Nebr.); AlexaFluor-555-conjugated anti-rabbit, Invitrogen (Carlsbad, Calif.). Recombinant murine TNF, IFN-γ, and EGF were from Peprotech. HRG-1β and anti-caspase antibody were from R&D Systems (Minneapolis, Minn.). Recombinant NRG4 [A1/A2 ectodomain sequence (Hayes, N. V., Newsam, R. J., Baines, A. J., and Gullick, W. J. (2008) *Oncogene* 27, 715-720)] was synthesized by Genscript Corp (Piscataway, N.J.). LY294002 (PI 3-kinase inhibitor) was purchased from Cell Signaling.

Animals—

All animal use was approved and monitored by the Children's Hospital Los Angeles Institutional Animal Care and Use Committee. Experiments used 6-8 week old male C57Bl/6J mice (The Jackson Laboratory, Bar Harbor, Me.). Cytokines, growth factors, and inhibitors were given by intraperitoneal injection. 24 h after injections, mice were sacrificed and colons collected either for fixation and embedding or for epithelial lysates. For the latter, colons were incubated in Cell Recovery Solution (BD Biosciences, San Jose, Calif.) for 1 h at 4° C.; crypts were released by vigorous shaking and collected by centrifugation, similar to as previously described (Whitehead, R. H., and Robinson, P. S. (2009) *American journal of physiology. Gastrointestinal and liver physiology* 296, G455-460). Collected crypts were lysed and processed similar to cultured cells as below. For murine colitis, IL-10$^{-/-}$ mice on C57Bl/6 background were maintained unchallenged until 32-36 weeks of age, at which point knockout mice but not wild-type animals have extensive inflammatory cytokine-driven colitis (Kuhn, R., Lohler, J., Rennick, D., Rajewsky, K., and Muller, W. (1993) *Cell* 75, 263-274).

Immunofluorescence and Histochemical Analysis—

Tissues and cells were fixed with 4% paraformaldehyde (Electron Microscopy Sciences, Hatfield, Pa.). Immunostaining was performed using standard techniques on 4-6 μM paraffin-embedded sections or fixed YAMC-B4 cells, using the manufacturers' suggestions for antibody dilutions. For immunofluorescence, slides were mounted with Vectashield medium containing DAPI (Vector Laboratories, Burlingame, Calif.). For immunohistochemistry, diaminobenzidine substrate was from Sigma Corp (St. Louis, Mo.) and sections were counterstained with methyl green (Dako Corp).

Cell Lysates and Western Blot Analysis—

Cell lysates were extracted in modified RIPA buffer as previously described (Frey, M. R., Dise, R. S., Edelblum, K. L., and Polk, D. B. (2006) *Embo J* 25, 5683-5692), cleared by centrifugation, and boiled in Laemmli sample buffer. Samples were separated on SDS-polyacrylamide gels (6-10% as appropriate), blotted on PVDF membranes, and subjected to quantitative immunoblot using the Li-Cor Odyssey infrared detection system. Equal loading was monitored by immunoblots for actin and at least one additional protein.

Apoptosis Assays—

Apoptosis was stimulated in cell culture by 6 h exposure to a cytokine cocktail containing TNF (100 ng/ml) plus IFN-γ (150 units/ml), with or without recombinant NRG4 (100 ng/ml). In some experiments, LY294002 (PI3K inhibitor, 5 μM) was also used. Cells were fixed in 4% paraformaldehyde and immunostained for cleaved caspase-3.

For apoptosis analysis in vivo, mice were injected i.p. with PBS/vehicle, TNF (250 μg/kg) plus IFN-γ (250 units/g), NRG4 (100 μg/kg), or NRG4 plus TNF and IFN-γ. In some experiments, LY294002 (50 mg/kg) was included. After 24 h, mice were euthanized and colons were removed and either fixed or used to make mucosal homogenates. Apoptosis was detected by in situ oligo ligation (ISOL; EMD Millipore, Billerica, Mass.) staining for DNA fragmentation on sections of paraffin-embedded tissue, and by cleaved caspase-3 western blot on homogenates.

Proliferation Assays—

Proliferative index in fixed colon specimens was assessed by immunohistochemical stain for Ki-67. In vitro, cells were exposed to vehicle or growth factors for 24 h, then labeled with 5-ethynyl-2-deoxyuridine (EdU) for 2 h and fixed. Nuclei were marked with DAPI, and incorporated EdU was detected using a Click-iT EdU kit (Invitrogen).

Cell Migration/Restitution—

Cells grown on fibronectin-coated plates were subjected to multiple circular wounds with a rotating silicone probe as previously described (Corredor, J., Yan, F., Shen, C. C., Tong, W., John, S. K., Wilson, G., Whitehead, R., and Polk, D. B. (2003) *American journal of physiology. Cell physiology* 284, C953-961). Cultures were photographed immediately and 8 h after wounding; % closure was determined by measuring wounds in Image.

RNA Isolation and RT-PCR Detection of ErbB Ligands—

Total RNA from flash-frozen mouse colon or isolated epithelial cells was purified with RNeasy columns (Qiagen, Valencia, Calif.) including on-column DNase treatment. cDNA was synthesized from 1 μg RNA with iScript (Bio-Rad, Hercules, Calif.), amplified by standard PCR techniques using previously described primers (Huotari, M. A., Miettinen, P. J., Palgi, J., Koivisto, T., Ustinov, J., Harari, D., Yarden, Y., and Otonkoski, T. (2002) *Endocrinology* 143, 4437-4446), and visualized by gel electrophoresis.

Real-Time Quantitative PCR (qPCR) Analysis of NRG4 in IBD—

NRG4 and HRG-1β expression levels were determined in human IBD using TaqMan gene expression assays (Life Technologies, Grand Island, N.Y.) on TissueScan Crohn's/Colitis qPCR Arrays [OriGene Technologies, Rockville Md.; these specimens were fully de-identified before receipt, and the study was reviewed by the CHLA Institutional Review Board and determined to not qualify as "human subject" research per § 46.102(f)(Wilson, K. J., Gilmore, J. L., Foley, J., Lemmon, M. A., and Riese, D. J., 2nd. (2009) *Pharmacology & therapeutics* 122, 1-8)]. Relative mRNA levels were calculated using the $2^{-\Delta\Delta C_T}$ method with β-actin as the reference; validity of the reference was confirmed by comparing to a second reference gene (β-glucuronidase).

Statistics and Replicates—

All data are representative of at least three independent experiments. Statistical analyses were performed with Prism software (GraphPad Inc., La Jolla, Calif.). Statistical significance was assessed by ANOVA analysis with Tukey post-test. Error bars indicate standard error of means.

Example 2

NRG4 Blocks Inflammatory Cytokine Induced Colonocyte Apoptosis Both In Vitro and In Vivo Multiple ErbB family ligands are expressed in the colon (Table 1). RNA was prepared from flash-frozen whole mouse colon or isolated colon epithelium, then subjected to RT-PCR analysis for presence of the indicated ligands (receptor binding specificities indicated in parentheses of Table 1).

TABLE 1

ErbB ligands expressed in mouse colon

| Ligand | Whole Colon | Isolated epithelial cells |
|---|---|---|
| EGF (EGFR) | + | − |
| HB-EGF (EGFR, ErbB4) | + | + |
| Betacellulin (EGFR, ErbB4) | + | − |
| NRG4 (ErbB4) | + | − |
| HRG-1β (ErbB3, ErbB4) | + | − |
| TGF-α (EGFR) | + | + |

Of these, only NRG4 is thought to be specific for ErbB4 versus other family members (Harari, D., Tzahar, E., Romano, J., Shelly, M., Pierce, J. H., Andrews, G. C., and Yarden, Y. (1999) *Oncogene* 18, 2681-2689); thus, we used this ligand to define the role of ErbB4 activation in colonic epithelial biology. ErbB4 is expressed throughout the intestinal tract (FIG. 1A) and is induced in colon epithelial cells by inflammation. Homegenates of 6-weeks old male C57/BL6 duodenum (Duo), jejunum (Jej), ileum (Ile), proximal colon (PC) and distal colon (CD) were analyzed by Western blot for exoression of ErbB4 and its specific ligand, NRG4. Both ErbB4 and NRG4 were expressed from duodenum to distal colon. Blots are representative of data from 3 mice.

Cultured mouse colonic epithelial cells expressing ErbB4 (YAMC-B4) cells were exposed to TNF (100 ng/ml) plus interferon (IFN)-γ (150 units/ml), with or without NRG4 (100 ng/ml). After 6 h, the cells were fixed and apoptosis was assessed by immunofluorescence analysis for cleaved caspase-3. When the YAMC-B4 cells were given 100 ng/ml NRG4, cells were protected from apoptosis induced by the 6 h exposure to the cytokine cocktail containing TNF (100 ng/ml) and IFN-γ (150 U/ml), as measured by immunofluorescence analysis for cleaved caspase-3 (FIG. 1B; 2.7-fold decrease with cytokines plus NRG4 vs. cytokines alone, p<0.03). Similar results were obtained by TUNEL assay.

Figure 2:
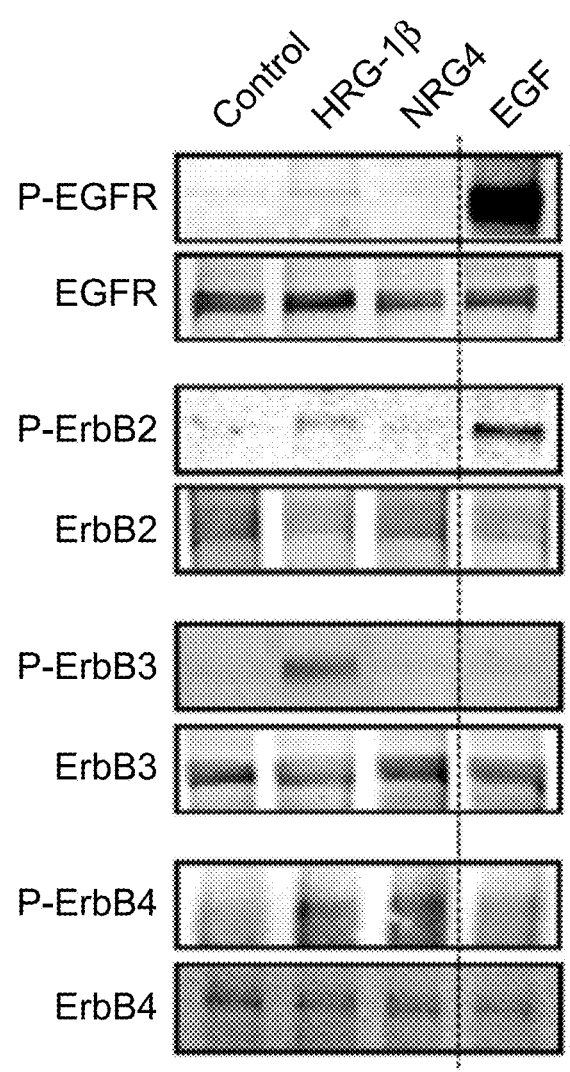
FIG. 2 depicts, in accordance with an embodiment of the invention that ErbB4, but not ErbB1-3, is stimulated by NRG4 in colonocytes.

To confirm that this result was specifically due to ErbB4 stimulation, YAMC-B4 cells were exposed to HRG-1β (100 ng/ml), NRG4, or EGF (10 ng/ml) for 10 min. Phosphorylation of EGFR, ErbB2, ErbB3, and ErbB4 was determined by western blot analysis of cell lysates using phospho-specific antibodies. Blots are representative of results at least 3 independent experiments. While the positive controls EGF and HRG-1β stimulated phosphorylation of multiple ErbBs (FIG. 2), NRG4 activated only ErbB4, confirming that NRG4 is an ErbB4-specific ligand.

Figure 3:
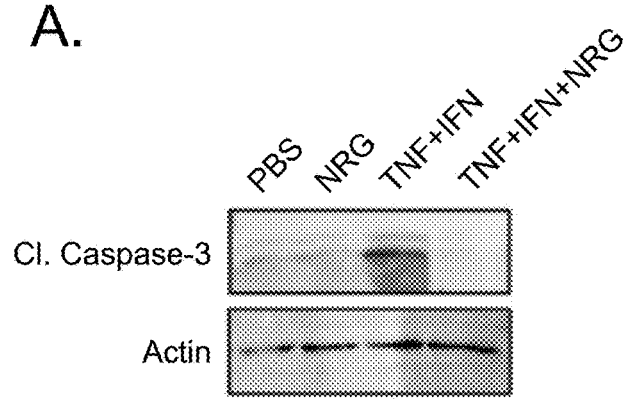
FIG. 3 depicts, in accordance with an embodiment of the invention that NRG4 blocks cytokine-induced apoptosis in vivo. Mice were injected i.p. with TNF (250 µg/kg) plus IFN-γ (250 units/g), with or without NRG4 (100 µg/kg). After 24 h, colons were excised. Apoptosis was assessed by (A, B) western blot for cleaved caspase-3 on mucosal scrapings (graph in B is quantification of blots from 4 mice per condition) and (C, D) ISOL stain (images in C show representative labeled cells) on sections of fixed, paraffin-embedded tissue.
Figure 3:
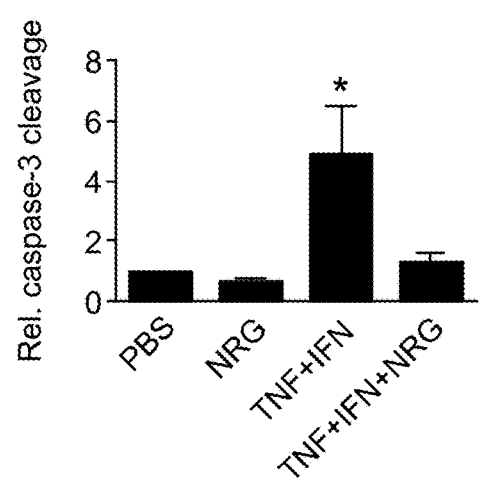
Figure 3:
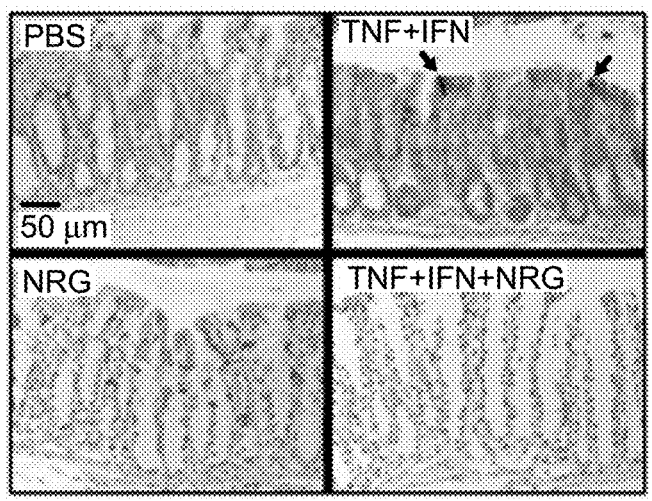
Figure 3:
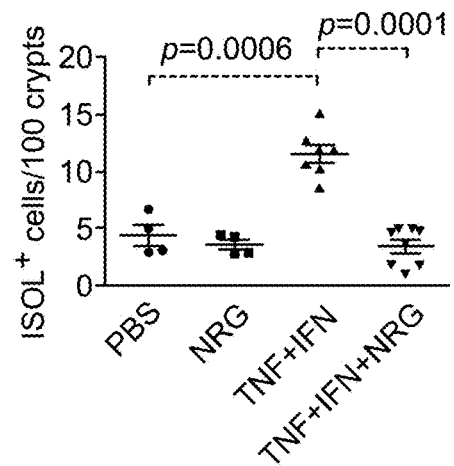

To translate these results into an in vivo setting, we injected 6-8 week old C57Bl/6 mice intraperitoneally with 250 µg/kg TNF plus 250 U/g of IFN-γ, with or without NRG4 (100 µg/kg). 24 hours after injections, colons were harvested. Apoptosis assessed by Western blot analysis for cleaved caspase-3 on isolated epithelial cells determined that NRG4 blocked cytokine-induced apoptosis in vivo (FIG. 3A, B; 3.6-fold decrease, p=0.012). Similar results were obtained with western blot analysis for cleaved poly (ADP-ribose) polymerase. ISOL staining on sections of fixed, paraffin-embedded colons also showed a significant reduction in apoptosis with NRG4 (FIG. 3C, D; 3.1-fold decrease, p<0.0001). Together, the data herein show that NRG4 activation of ErbB4 in colon epithelial cells protects them from cytokine-induced apoptosis both in cell culture and in vivo.

Example 3

Colonocyte Proliferation and Migration are not Affected by NRG4

Most ErbB ligands stimulate multiple cellular processes, including proliferation and migration, in colon epithelial cells (Frey, M. R., Golovin, A., and Polk, D. B. (2004) *J Biol Chem* 279, 44513-44521). To determine if NRG4 is similarly broad in its cellular effects, we subjected YAMC-B4 cells to proliferation assays in the presence of NRG4. After 24 h stimulation with NRG4, cellular uptake of the modified nucleoside EdU was not different from control, while in contrast EGF stimulated proliferation by 31.5% over control (FIG. 4A). In vivo, the number of Ki67-positive nuclei per crypt in PBS vs. NRG4-injected mice was not altered 24 h post-injection (FIG. 4B).

To test the potential effect of NRG4-ErbB4 signaling on cell motility, we used a modified scratch assay for restitution/migration (Corredor, J., Yan, F., Shen, C. C., Tong, W., John, S. K., Wilson, G., Whitehead, R., and Polk, D. B. (2003) *American journal of physiology. Cell physiology* 284, C953-961). Over an 8 h period, NRG4 had no effect on the rate at which YAMC-B4 cells moved into the denuded area of a culture plate (FIG. 4C), while in contrast EGF caused a 54% increase in migration over control. Together, these results indicate that, unlike many other growth factors, NRG4 selectively promotes colon epithelial cell survival without affecting cell proliferation or migration.

In the dextran sodium sulfate-induced model of acute murine colitis, NRG4 treatment reduces weight loss, colon shortening, and histologically detectable colonic damage (FIG. 4D). 6-8 week-old male C57/BL6 mice were given 3% DSS in drinking water for 7 days and injected daily with either PBS or NRG4 (100 µg/kg). Weight-loss was monitored over the course of the experiment (FIG. 4D(i)). On day 7, mice were sacrificed; colons were excised, rolled and fixed. H&E sections were scored by a pathologist blind to the experimental conditions using a scoring system adapted from that of Dielman et al. (Dieleman, L. A., et al., *Chronic experimental colitis induced by dextran sulphate sodium (DSS) is characterized by Th1 and Th2 cytokines*. Clinical and experimental immunology, 1998. 114(3): p. 385-91) (FIG. 4D(ii)). NRG4 is also protective in the small intestine in the formula feeding/hypoxia model of necrotizing enterocolitis. Together, these data indicate that NRG4 is protective in multiple intestinal injury models, possibly through inhibition of epithelial cell apoptosis.

Example 4

NRG4-ErbB4 Signaling Stimulates Akt Activation

To identify signaling pathways which could be involved in NRG4-stimulated cell survival, we exposed YAMC-B4 cells to NRG4 or EGF and prepared whole cell lysates for western blot analysis. NRG4 exposure (100 ng/ml, 10 min) resulted in phosphorylation of Akt but not ERK MAPK (FIG. 5A), in contrast to HRG-1β and EGF which activated both cascades. Furthermore, COX-2 expression, which is induced by either HRG-1β or EGF after 6 h exposure, and is required for cell survival induced by ErbB4-EGFR dimers (Frey, M. R., Hilliard, V. C., Mullane, M. T., and Polk, D. B. (2010) *Laboratory Investigation* 90, 1415-1424), was not induced by NRG4. Thus, NRG4 promotes cell survival through pathways at least partly distinct from those activated by other ligands. Similar to the cell culture data, western blot analysis of colon epithelial cells isolated from mice injected with NRG4 (with or without TNF plus IFN-γ) showed increased Akt phosphorylation versus controls (FIG. 5B); increased Akt phosphorylation was also detectable by immunofluorescence analysis on fixed colons from NRG4-injected mice (FIG. 5C).

Example 5

PI 3-Kinase/Akt Signaling is Necessary for NRG4-Induced Cell Survival In Vitro and In Vivo To test the role of PI 3-kinase/Akt signaling in NRG4-stimulated YAMC-B4 cell survival, we added the PI3K inhibitor LY294002 (5 µM) to cultures incubated with TNF plus IFN-γ or TNF plus IFN-γ and NRG4. Immunofluorescence analysis for cleaved caspase-3 showed that the PI3K inhibitor reversed NRG4's protective effect in YAMC-B4 cells (FIG. 6A). In vivo, LY294002 injection (50 µg/kg) reversed NRG4's blockade of cytokine-induced colon epithelial apoptosis as measured by ISOL stain (FIG. 6B).

Example 6

NRG4 Expression is Reduced in Crohn's Disease and Ulcerative Colitis

Figure 7:
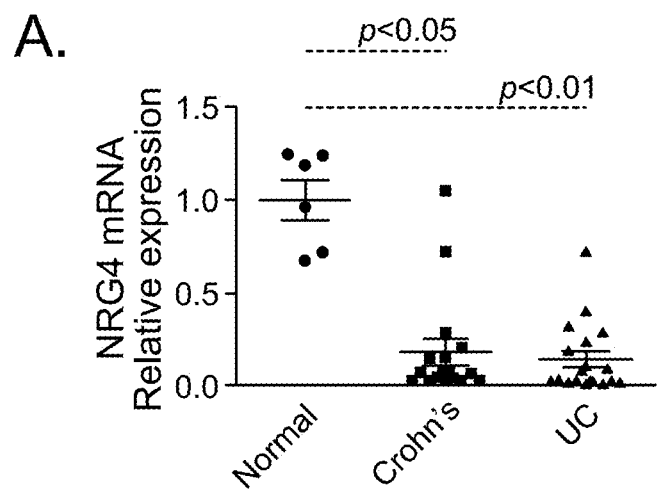
FIG. 7 depicts, in accordance with an embodiment of the invention that NRG4 levels are decreased in human inflammatory bowel disease. (A,B) qPCR analysis for (A) NRG4 and (B) HRG-1β gene expression was performed on TissueScan Crohn's/Colitis qPCR Arrays. Relative mRNA levels were calculated using the $2^{-\Delta\Delta C_T}$ method with 13-actin as the reference. (C) Colonic homogenates from wild type controls (WT) or IL-10$^{-/-}$ mice were subjected to western blot analysis for ErbB4, phospho-ErbB4, and NRG4. Results shown are representative of 4 mice per genotype.
Figure 7:
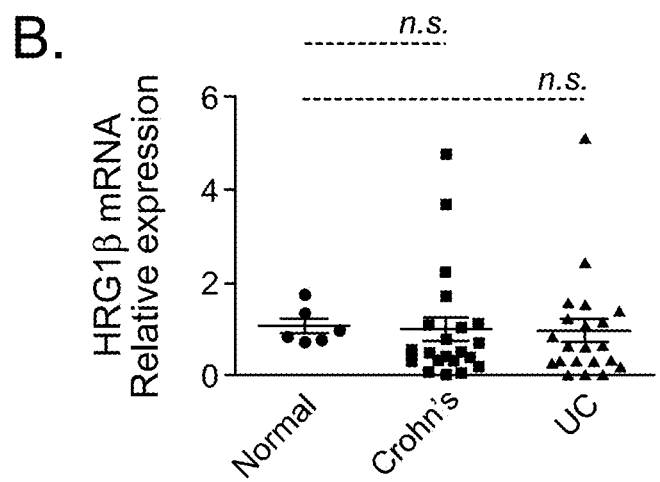
Figure 7:
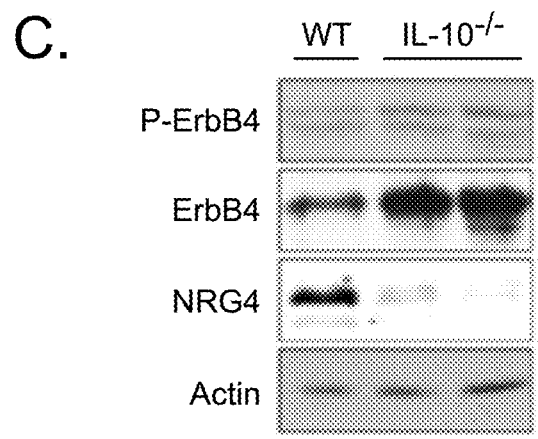

To investigate the potential clinical relevance of a colon epithelial cell survival pathway driven by NRG4, we studied the ligand's expression in human inflammatory bowel disease. qPCR analysis of biopsies from Crohn's disease & ulcerative colitis patients showed 5.6 (p<0.05) and 7.1 (p<0.01) fold reductions, respectively, in NRG4 expression versus uninflamed controls (FIG. 7A). In contrast, we detected no change in expression of the shared ErbB3/ErbB4 ligand HRG-1β (FIG. 7B), suggesting a selective loss of the specific ErbB4 ligand only. In the IL-10$^{-/-}$ mouse model of chronic colitis (Kuhn, R., Lohler, J., Rennick, D., Rajewsky, K., and Muller, W. (1993) *Cell* 75, 263-274), NRG4 protein levels were reduced in colitic animals as determined by western blot analysis of intestinal homogenates (FIG. 7C). Furthermore, while ErbB4 expression was elevated in the inflamed colons, similar to what we previously reported for human IBD or murine DSS colitis (Frey, M. R., Edelblum, K. L., Mullane, M. T., Liang, D., and Polk, D. B. (2009) *Gastroenterology* 136, 217-226), ErbB4 phosphorylation was not increased (FIG. 7C). Thus, loss of the NRG4 ligand is associated with failure to activate ErbB4 despite upregulation of the receptor.

Example 7

Figure 8:
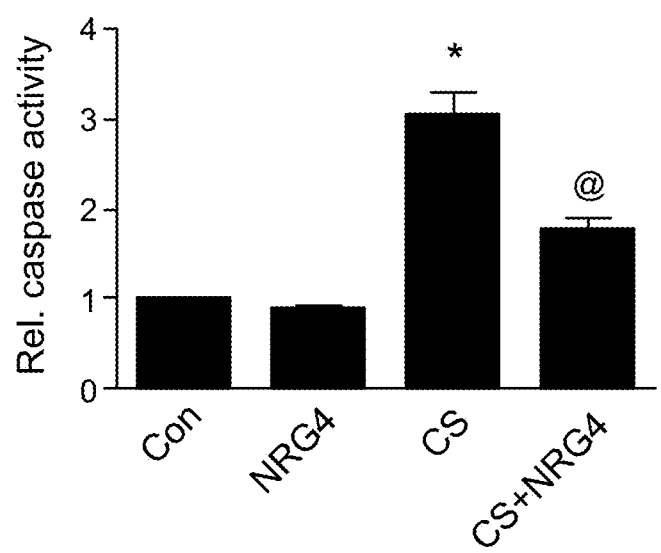
FIG. 8 depicts, in accordance with an embodiment of the invention that in rat ileal epithelial cells, *Cronobacter sakazakii*-induced apoptosis is attenuated by NRG4.
Figure 9:
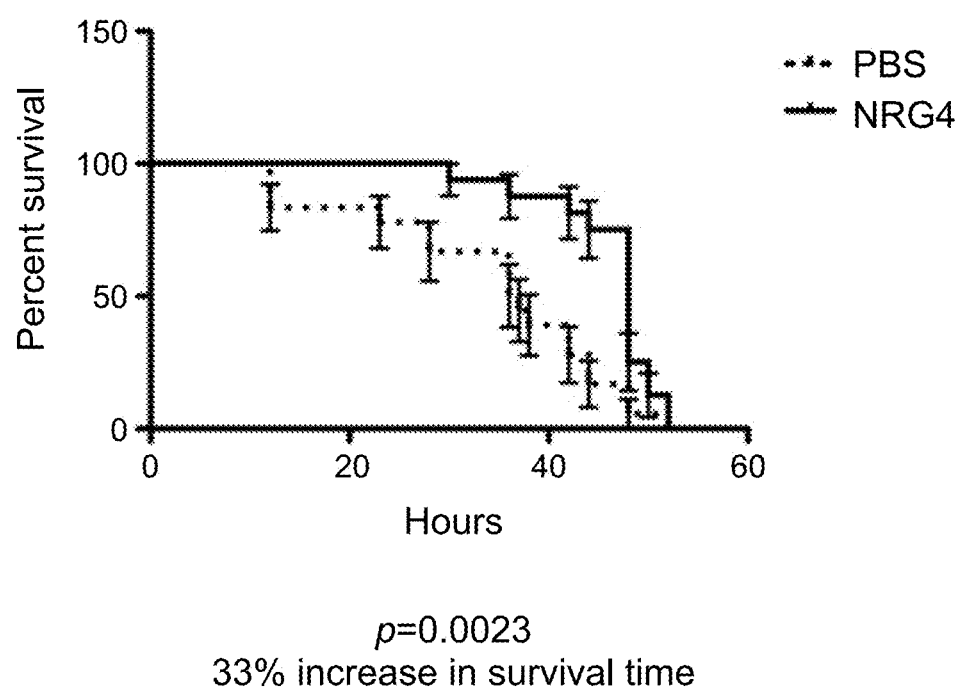
FIG. 9 depicts, in accordance with an embodiment of the invention that rat pups are resistant to experimental NEC when treated with NRG4.

*Cronobacter sakazakii* are used as the damaging agent in an infectious necrotizing enterocolitis (NEC) rat model, and has been implicated in NEC outbreaks driven by contaminated formula. In vitro, it causes apoptosis of colon epithelial cells. NRG4 inhibits CS-induced cell death. FIG. 8 shows that NRG4 attenuates *Cronobacter sakazakii* induced apoptosis in cultured rat intestinal epithelial cells. FIG. 9 shows that rat pups are resistant to experimental NEC when treated with NRG4. This survival curve demonstrates that in the hypoxia/hypothermia model of NEC in rat pups (modeled after Barlow et al., Journal of Pediatric Surgery Volume 9, Issue 5, October 1974, Pages 587-595), the pups survive longer if NRG is administered by gavage with each feed.

Example 8

Figure 4:
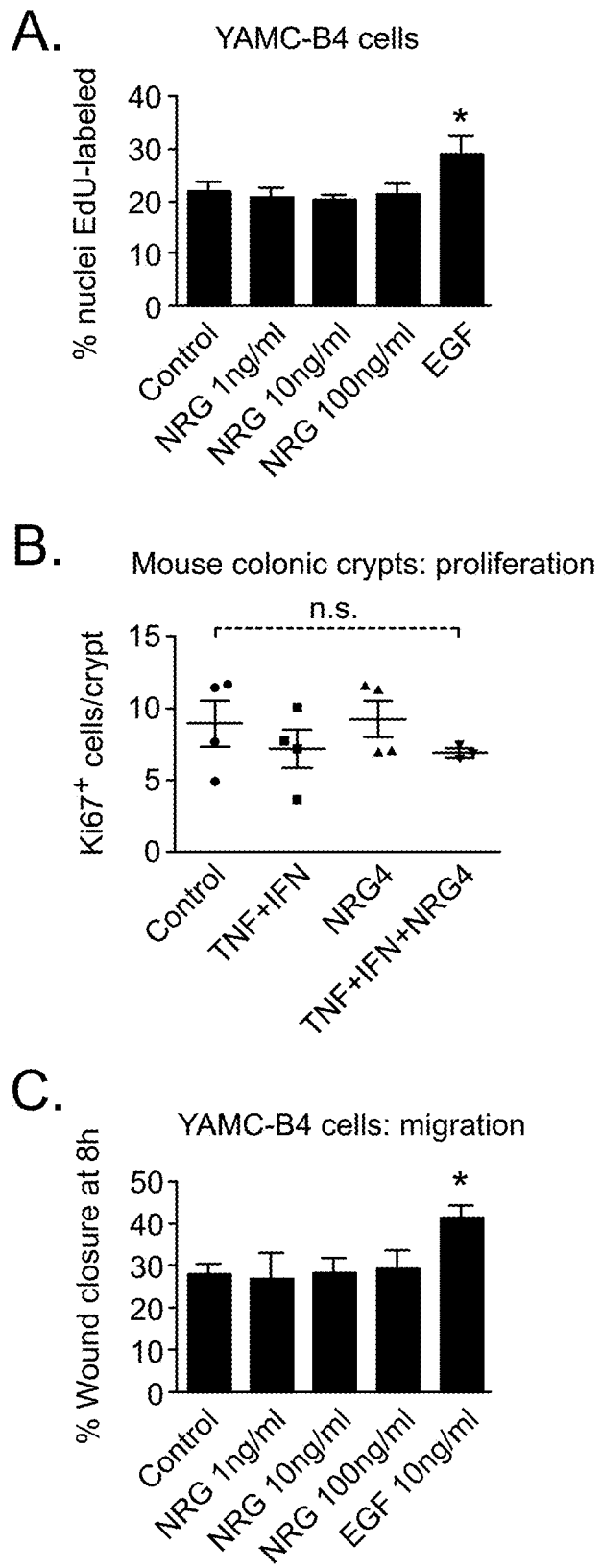
FIG. 4 depicts, in accordance with an embodiment of the invention that NRG4 does not stimulate colonocyte proliferation or migration. (A) Young adult mouse colon epithelial cells expressing ErbB4 (YAMC-B4 cells) were given NRG4 or epidermal growth factor (EGF, positive control for cell stimulation) for 24 h, then labeled with EdU to determine proliferative index. Graph depicts results from 3 independent experiments. *, p<0.01 vs. all other columns. (B) Fixed colon sections from PBS- or NRG4-injected mice were immunostained for the proliferative marker Ki-67, and number of labeled cells per crypt counted. Data points are average cells/crypt in individual mice. (C) YAMC-B4 cells were subjected to an 8 h migration/restitution assay in the presence of NRG4 or EGF. *, p<0.01 vs. all other columns. (D) Exogenous NRG4 is protective in acute DSS colitis.
Figure 4:
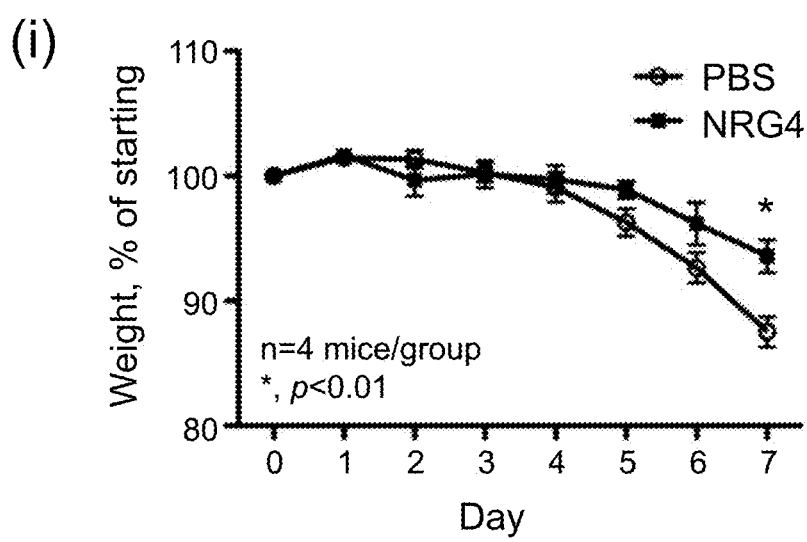
Figure 4:
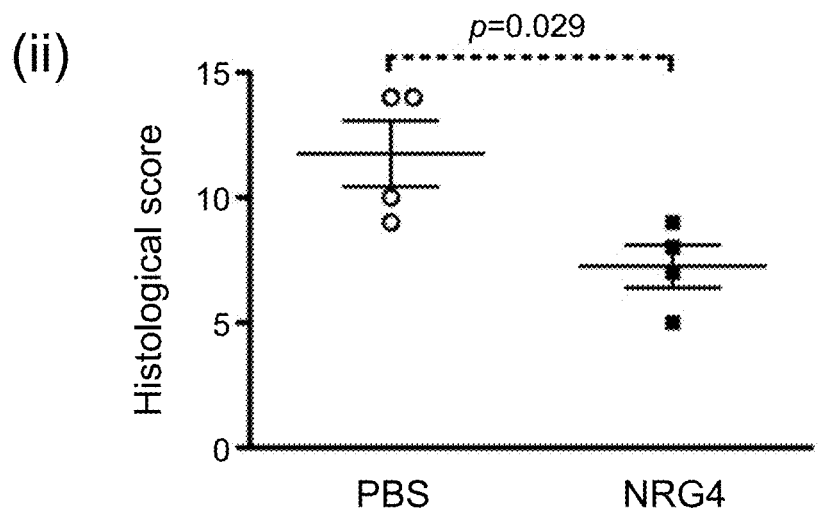
Figure 5:
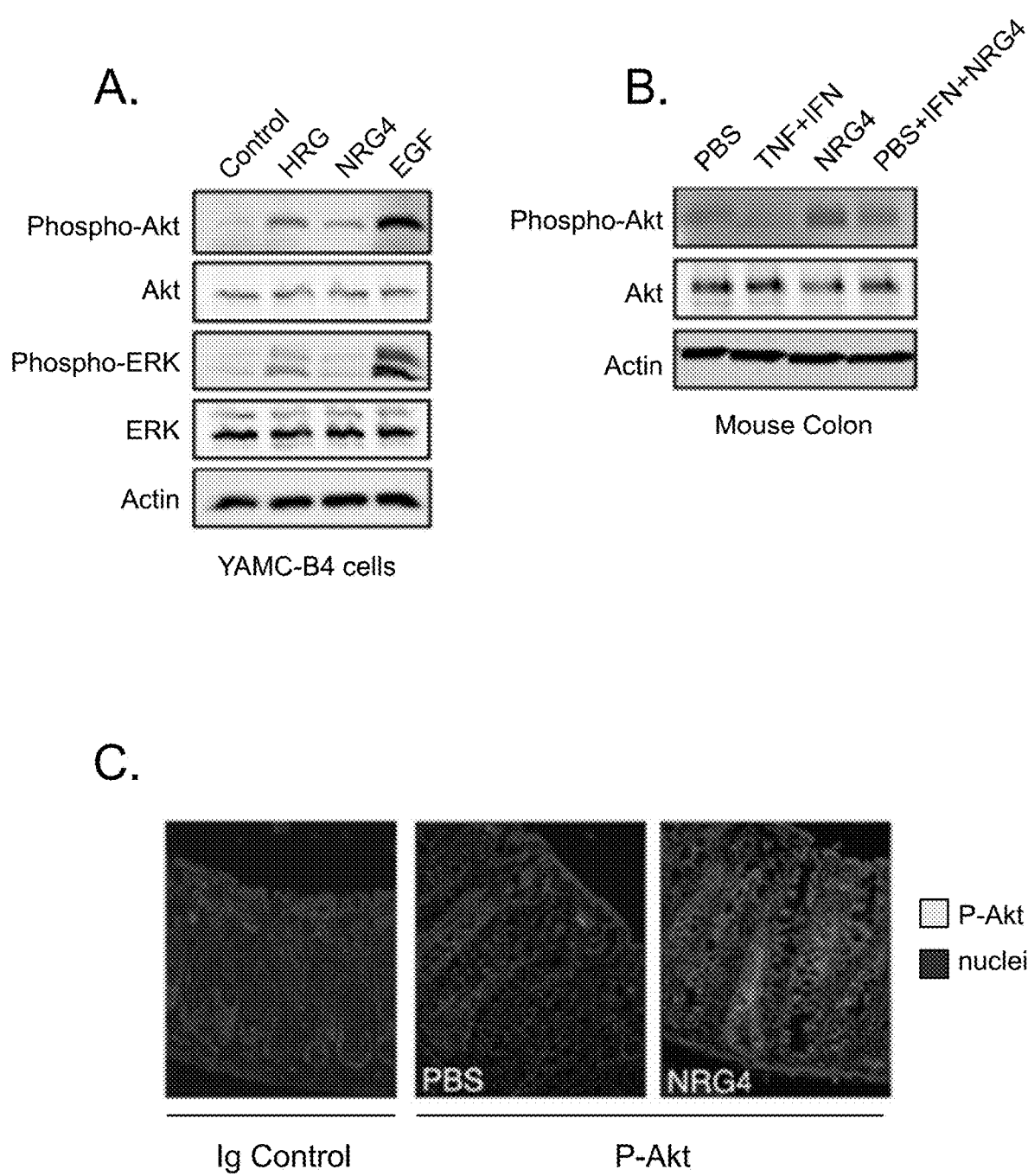
FIG. 5 depicts, in accordance with an embodiment of the invention that Akt phosphorylation is stimulated by NRG4 in vitro and in vivo. (A) YAMC-B4 cells were stimulated with NRG4 for 10' and whole cell lysates were prepared. (B) Mice were injected with NRG4 with or without TNF+IFN-γ; after 24 h epithelial homogenates were prepared. Expression and phosphorylation of indicated molecules were determined by western blot analysis. (C) Akt phosphorylation in fixed, paraffin-embedded colonic tissue was assessed by immunofluorescence analysis. Data are representative of at least 3 independent experiments or mice per condition.
Figure 6:
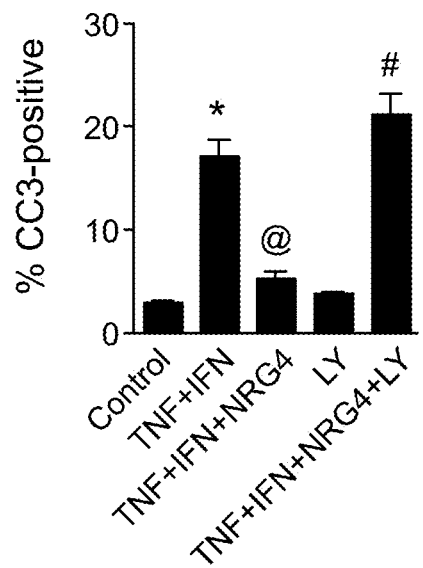
FIG. 6 depicts, in accordance with an embodiment of the invention that PI3K inhibitor blocks NRG4 antiapoptotic effects. (A) YAMC-B4 cells were exposed to TNF+IFN-γ, with or without NRG4 and/or inhibitor to PI3K (LY294002). After 6 h, cells were fixed and apoptosis was assessed by immunofluorescent staining for cleaved caspase-3. Data are representative of 4 independent experiments. (B) Mice were injected with TNF+IFN-γ, with or without NRG4 and/or inhibitor to PI3K (LY294002). After 24 h, colons were fixed and apoptosis was quantified by ISOL stain.
Figure 6:
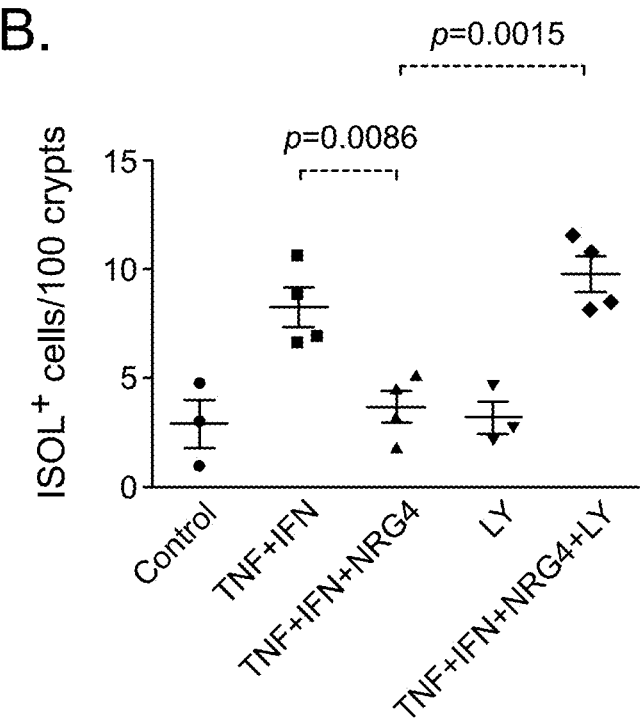

Previous investigation into the role of the ErbB4 receptor tyrosine kinase in epithelial tissues has largely relied on results using ligands such as HB-EGF or HRG-1I (Frey, M. R., Hilliard, V. C., Mullane, M. T., and Polk, D. B. (2010) *Laboratory Investigation* 90, 1415-1424; Ni, C. Y., Murphy, M. P., Golde, T. E., and Carpenter, G. (2001) *Science* 294, 2179-2181), which also activate other ErbB family members (e.g., see FIG. 2). Herein, the inventor used NRG4 to specifically activate ErbB4 in colonocytes. The results show that ErbB4 activation in the absence of detectable phosphorylation of EGFR, ErbB2, or ErbB3 results in an increase in anti-apoptotic signaling both in vitro (FIG. 1) and in vivo (FIG. 3), with no change in cell proliferation or migration (FIG. 4). NRG4-induced suppression of apoptosis was dependent on the PI3K/Akt pathway (FIGS. 5 & 6). Thus, selective activation of ErbB4 with NRG4 may be a specific cell survival stimulus.

The data show phosphorylation of ErbB4, but not other ErbBs, in response to NRG4. Taken together with previous observations that NRG4 does not directly bind other receptors (Haran, D., Tzahar, E., Romano, J., Shelly, M., Pierce, J. H., Andrews, G. C., and Yarden, Y. (1999) *Oncogene* 18, 2681-2689), this suggests that ErbB4 homodimers are the effective mediator of its signaling. It is formally possible that asymmetric heterodimers (Monsey, J., Shen, W., Schlesinger, P., and Bose, R. (2010) *J Biol Chem* 285, 7035-7044; Macdonald-Obermann, J. L., Piwnica-Worms, D., and Pike, L. J. (2012) *Proc Natl Acad Sci USA* 109, 137-142) play a role in NRG4-induced effects, but we have not been able to detect NRG4-driven association of ErbB4 with other ErbBs. Regardless, in the absence of their phosphorylation it seems unlikely that ErbB1-3 play a significant role in downstream signaling in response to NRG4.

In this context, it is interesting that NRG4, unlike other ErbB ligands, promotes survival but not proliferation or migration of colon epithelial cells. In proteomic peptide-binding studies, ErbB4 associates with a more restricted suite of SH2-containing targets than EGFR, ErbB2, or ErbB3 (Kaushansky, A., Gordus, A., Budnik, B. A., Lane, W. S., Rush, J., and MacBeath, G. (2008) *Chem Biol* 15, 808-817). Furthermore, in the current report we show that specific ErbB4 activation elicits only a subset of the downstream signaling, including activation of Akt, but not ERK MAPK, compared to other ErbB ligands including HRG-1β [FIG. 5 and (12)], HB-EGF (26), and TGF-α (McCole, D. F., Keely, S. J., Coffey, R. J., and Barrett, K. E. (2002) *J Biol Chem* 277, 42603-42612). These observations are consistent with our data showing that NRG4 is selectively a survival factor, thus positioning ErbB4 as the only family member that can promote cell survival without affecting proliferation or migration. Interestingly, some pathways (e.g., COX-2) required for the cell survival response to HRG-1β are apparently not necessary in the case of NRG4; whether the absence of proliferative signaling (e.g. ERK) with NRG4 narrows the requirement for cell protection from apoptosis, or in contrast an overlapping but distinct set of alternative pathways are activated but the different ligands, is an area of ongoing study in our laboratory.

Specificity for cell survival but not cell division is in agreement with the apparent lower oncogenic potential reported in the literature for ErbB4 versus other receptor tyrosine kinases. While increased levels or activity of EGFR, ErbB2, or ErbB3 are in general associated with increased tumor growth, the role of ErbB4 is less certain. It is overexpressed in endometrial (Srinivasan, R., Benton, E., McCormick, F., Thomas, H., and Gullick, W. J. (1999) *Clin Cancer Res* 5, 2877-2883) and non-small cell lung cancers (Starr, A., Greif, J., Vexler, A., Ashkenazy-Voghera, M., Gladesh, V., Rubin, C., Kerber, G., Marmor, S., Lev-Ari, S., Inbar, M., Yarden, Y., and Ben-Yosef, R. (2006) *Int J Cancer* 119, 269-274), while in contrast transitional cell carcinoma of the bladder (Memon, A. A., Sorensen, B. S., Melgard, P., Fokdal, L., Thykjaer, T., and Nexo, E. (2004) *Br J Cancer* 91, 2034-2041; Rotterud, R., Nesland, J. M., Berner, A., and Fossa, S. D. (2005) *BJU Int* 95, 1344-1350) and prostate cancer (Edwards, J., Traynor, P., Munro, A. F., Pirret, C. F., Dunne, B., and Bartlett, J. M. (2006) *Clin Cancer Res* 12, 123-130; Robinson, D., He, F., Pretlow, T., and Kung, H. J. (1996) *Proc Natl Acad Sci USA* 93, 5958-5962) show either no correlation between ErbB4 levels and tumor behavior or an association between expression and good prognosis. Studies on in breast cancer have yielded a contradictory literature, with different papers suggesting ErbB4 expression is associated with either poor (Srinivasan, R., Gillett, C. E., Barnes, D. M., and Gullick, W. J. (2000) *Cancer Res* 60, 1483-1487; Junttila, T. T., Sundvall, M., Lundin, M., Lundin, J., Tanner, M., Harkonen, P., Joensuu, H., Isola, J., and Elenius, K. (2005) *Cancer Res* 65, 1384-1393) or favorable (Tovey, S. M., Witton, C. J., Bartlett, J. M., Stanton, P. D., Reeves, J. R., and Cooke, T. G. (2004) *Breast Cancer Res* 6, R246-251; Witton, C. J., Reeves, J. R., Going, J. J., Cooke, T. G., and Bartlett, J. M. (2003) *J Pathol* 200, 290-297) outcome. These apparently inconsistent findings may be in part explained by our results, if ErbB4 signaling per se does not necessarily promote cell proliferation. ErbB4 activation by HRG-1I, which stimulates multiple receptors, does activate cancer-associated pathways such as COX-2, but this response is dependent on partnering with EGFR (Frey, M. R., Hilliard, V. C., Mullane, M. T., and Polk, D. B. (2010) *Laboratory Investigation* 90, 1415-1424). It may be that ErbB4 only promotes tumorigenesis in partnership with other, more frankly oncogenic, ErbBs, as in for example ErbB2/4 heterodimerization observed in late-stage colorectal cancers (Lee, J. C., Wang, S. T., Chow, N. H., and Yang, H. B. (2002) *Eur J Cancer* 38, 1065-1071) or the results of Lee and colleagues identifying ErbB3/4 dimers as tumor promoters (Lee, D., Yu, M., Lee, E., Kim, H., Yang, Y., Kim, K., Pannicia, C., Kurie, J. M., and Threadgill, D. W. (2009) *J Clin Invest* 119, 2702-2713).

The ability to block cytokine-stimulated colonocyte apoptosis, combined with the decreased risk for proliferative disorders compared with other growth factors, makes NRG4 an attractive potential therapy for conditions such as IBD which involve elevated apoptosis in the epithelium of the small intestine or colon (Qiu, W., Wu, B., Wang, X., Buchanan, M. E., Regueiro, M. D., Hartman, D. J., Schoen, R. E., Yu, J., and Zhang, L. (2011) *J Clin Invest* 121, 1722-1732; Di Sabatino, A., Ciccocioppo, R., Luinetti, O., Ricevuti, L., Morera, R., Cifone, M. G., Solcia, E., and Corazza, G. R. (2003) *Diseases of the colon and rectum* 46, 1498-1507). As ErbB4 has a number of biochemical features (including being the sole receptor for NRG4) that distinguish it from other ErbB family members (Carpenter, G. (2003) *Exp Cell Res* 284, 66-77), it is a unique and specific signaling target. In this regard, the observations that (a) NRG4 is deficient in both human IBD and murine colitis (FIG. 7A), and (b) although ErbB4 expression is elevated in the IL-10$^{-/-}$ murine colitis model, it is not phosphorylated/activated (FIG. 7C), raise the possibility that NRG4 down-regulation may lead to deficient epithelial cell survival signaling despite ErbB4 up-regulation. Consistent with this possibility, recent work from Feng and colleagues showed loss of NRG4 in a model of total parenteral nutrition (Feng, Y., and Teitelbaum, D. H. (2012) *American journal of physiology, gastrointestinal and liver physiology* 302, G236-249), which is associated with increased inflammatory cytokines and decreased Akt phosphorylation (Feng, Y., Ralls, M. W., Xiao, W., Miyasaka, E., Herman, R. S., and Teitelbaum, D. H. (2012) *Annals of the New York Academy of Sciences* 1258, 71-77). A dysregulated NRG4/ErbB4 balance and an altered ratio between NRG4 and other ErbB ligands may be important features of IBD which can be addressed with exogenous ligand.

The data herein show that selective activation of the ErbB4 receptor tyrosine kinase with its specific ligand NRG4 is a survival signal in colon epithelial cells. This pathway activates PI3K/Akt signaling and blocks inflammatory cytokine-induced apoptosis without affecting cell proliferation or migration. However, this pathway is deficient in IBD due to a loss of the ligand. Our observations underscore the unique properties of ErbB4 compared with other ErbB family members, and suggest that selective ErbB4 activation represents a divergent branch of receptor tyrosine kinase signaling with potential therapeutic use in injury or inflammatory diseases.

Various embodiments of the invention are described above. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method for screening for an activator of ErbB4 that increases phosphorylation of ErbB4 on ErbB4-positive cells and inhibits apoptosis of the ErbB4-positive cells, comprising:
    contacting a molecule of interest with ErbB4-positive cells,
    measuring an amount of phosphorylation of ErbB4 on the ErbB4-positive cells before the contact with the molecule of interest,
    measuring an amount of phosphorylation of ErbB4 on the ErbB4-positive cells in the presence of the molecule of interest,
    separately contacting the ErbB4-positive cells with a damaging agent selected from the group consisting of tumor necrosis factor (TNF), interferon gamma (IFN-γ), *Cronobacter sakazakii*, and a combination thereof,
    measuring an amount of apoptosis of the ErbB4-positive cells in the presence of the damaging agent but absent the molecule of interest,
    measuring an amount of apoptosis of the ErbB4-positive cells in the presence of the damaging agent and the molecule of interest,
    wherein an increase in the amount of phosphorylation of the ErbB4 in the presence of the molecule of interest relative to the amount before the contact with the molecule of interest and a decrease in the amount of apoptosis of the ErbB4-positive cells in the presence of the damaging agent and the molecule of interest relative to the amount in the presence of the damaging agent but absent the molecule of interest is indicative that the molecule of interest is an activator of ErbB4 that increases phosphorylation of ErbB4 on the ErbB4-positive cells and inhibits apoptosis of the ErbB4-positive cells,
    wherein the ErbB4-positive cells comprise epithelial cells, colonocytes, Paneth cells, or a combination thereof.

2. The method of claim 1, wherein the activator of ErbB4 is selected from the group consisting of a small molecule, a polypeptide, a peptide, and an antibody or a fragment thereof.

3. The method of claim 1, further comprising measuring the phosphorylation of ErbB1, ErbB2 and ErbB3 of the ErbB4-positive cells in the presence of the molecule of interest, wherein the molecule of interest indicated to be the activator of ErbB4 does not phosphorylate ErbB1 (EGFR), ErbB2, or ErbB3.

4. The method of claim 1, wherein measuring the amount of phosphorylation of the ErbB4 comprises using an immunoassay for phosphor-ErbB4.

5. The method of claim 1, wherein the ErbB4-positive cells comprise colonic epithelial cells.

6. The method of claim 1, wherein the increase in the amount of phosphorylation of ErbB4 in the presence of the molecule of interest is at least 10% of the amount of phosphorylation of ErbB4 in the presence of Neuregulin-4.

7. The method of claim 1, wherein the ErbB4-positive cells are epithelial cells.

8. The method of claim 1, wherein measuring the amount of phosphorylation, the amount of apoptosis, or both comprises performing an assay selected from the group consisting of microarray assay, quantitative polymerase chain reaction (PCR), Northern blot assay, Southern blot assay, Western blot assay, immunohistochemical assays, immunofluorescence analysis, assay that measure cell apoptosis, or a combination thereof.

9. The method of claim 1, wherein the molecule of interest binds ErbB4 in the contacting step, measured by a binding assay, gel retardation assay, or assay using a yeast two-hybrid system.

10. A method for screening for an activator of ErbB4 that increases phosphorylation of ErbB4 on ErbB4-positive cells and inhibits apoptosis of the ErbB4-positive cells from at least two molecules of interest, comprising:
    separately performing the steps according to claim 1 for each of the at least two molecules of interest,
wherein an increase in the amount of phosphorylation of ErbB4 of the ErbB4 in the presence of a molecule of interest relative to the amount before the contact with the molecule of interest and a decrease in the apoptosis of the ErbB4-positive cells in the presence of the damaging agent and the same molecule of interest relative to the amount in the presence of the damaging agent but absent the same molecule of interest is indicative that the same molecule of interest is an activator of ErbB4 that increases phosphorylation of ErbB4 on the ErbB4-positive cells and inhibits apoptosis of the ErbB4-positive cells.

11. The screening method of claim 10, wherein the at least two molecules of interest comprise more than about $10^4$ molecules of interest.

12. The screening method of claim 10, wherein the at least two molecules of interest comprise more than about $5 \times 10^4$ samples.

13. The screening method of claim 10, wherein the ErbB4-positive cells are epithelial cells.

14. The screening method of claim 10, wherein measuring the amount of phosphorylation, the amount of apoptosis, or both comprises performing an assay selected from the group consisting of microarray assay, quantitative polymerase chain reaction (PCR), Northern blot assay, Southern blot assay, Western blot assay, immunohistochemical assays, immunofluorescence analysis, assay that measure cell apoptosis, or a combination thereof.

15. The screening method of claim 10, wherein the molecule of interest binds ErbB4 in the contacting step, measured by a binding assay, gel retardation assay, or assay using a yeast two-hybrid system.

* * * * *